United States Patent [19]

Takasaki

[11] Patent Number: 4,855,232

[45] Date of Patent: Aug. 8, 1989

[54] METHOD FOR PRODUCTION OF GLUCOSE BY USE OF TRANSGLUCOSIDASE

[75] Inventor: Yoshiyuki Takasaki, Matsudo, Japan

[73] Assignees: Agency of Industrial Science & Technology; Ministry of International Trade & Industry, both of Tokyo, Japan

[21] Appl. No.: 176,312

[22] Filed: Mar. 31, 1988

[30] Foreign Application Priority Data

Feb. 9, 1988 [JP] Japan .................................. 63-28590

[51] Int. Cl.$^4$ ............................................. C12P 19/18
[52] U.S. Cl. ..................................... 435/97; 435/193; 435/814
[58] Field of Search .................................... 435/94–98, 435/814, 193

[56] References Cited

U.S. PATENT DOCUMENTS

| | | | |
|---|---|---|---|
| 2,891,869 | 6/1959 | Langlois | 435/96 |
| 2,967,804 | 1/1961 | Kerr | 435/96 |
| 3,303,102 | 2/1967 | Armbruster | 435/814 |
| 4,386,158 | 5/1983 | Shimizu | 435/97 |
| 4,487,831 | 12/1984 | Day | 435/815 |
| 4,649,058 | 3/1987 | Schwengers | 435/97 |
| 4,693,974 | 9/1987 | Schwengers | 435/87 |
| 4,734,364 | 3/1988 | Line | 435/814 |

*Primary Examiner*—Peter D. Rosenberg
*Attorney, Agent, or Firm*—Oblon, Spivak, McClelland, Maier & Neustadt

[57] ABSTRACT

A method for producing glucose at a high yield includes the step of saccharifying liquefied starch with a glucoamylase in the presence of a sugar transferase capable of the transfer reaction with a α-1,4-glucosidic bond.

10 Claims, 2 Drawing Sheets

METHOD FOR PRODUCTION OF GLUCOSE BY USE OF TRANSGLUCOSIDASE

BACKGROUND OF THE INVENTION

1. Field of the Invention

This invention relates to a method for the production of glucose by the use of the transglucosidase produced by genus Bacillus.

2. Prior Art Statement

Enzymes which effect transfer reaction of sugars are of two types, one relying on transferases and theother resorting to the reverse reaction of hydrolases. The transferases are classified by the kind of residue taking part on the transfer reaction into seven types. Among the transferases, those which take part in the transfer reaction of sugars are characterized by using oligosaccharides or polysaccharides as donors and transfer the residues thereof into other suitable acceptors such as monosaccharides, oligosaccharides, and various alcohols. They also include those enzymes which effect transfer of various saccharides such as glucose residues, xylose residues, and galactose residues. Alternatively, the transferases are classified by the kind of the bonding through which the transfer reaction takes place. As concrete examples of the industrial application of transferases, there can be cited the production of cyclodextrins by the use of a cyclodextringlucanotransferase, the production of coupling sugars by the use of the same enzyme, and the production of glucosylstevioside. As examples of the industrial application utilizing the reverse reaction of hydrolases, there can be cited the production of branched cyclodextrins by the use of pullulanase and the production of isomaltose by the use of glucoamylase.

The inventor has found that a certain sugar transferase manifests a conspicuous effect in increasing the yield of glucose in the hydrolysis of starch by the use of a glucoamylase. At present, glucose is produced by first liquefying starch (dextrin) with an α-amylase and then saccharifying the liquefied start with a glucoamylase.

Since the glucoamylass is capable of hydrolyzing both the α-1,4-glucosidic and α-1,6-glucosidic bonds of starch, it can hydrolyze starch substantially completely into glucose when the starch is in the form of a dilute solution. Since in the saccharification carried out on a commercial scale, starch is used in a high concentration of 30 to 35%, the produced glucose succumbs to polymerization induced as by the reverse synthetic action inherent in glucoamylase and, as a result, the yield of glucose generally falls in the range of 93 to 95%. The remainders are maltose, isomaltose, panose, and other oligosaccharides of still higher molecular weight. The idea of effecting further hydrolysis of these remaining oligosaccharides thereby attaining an addition to the yield of glucose has long been desired by the industry in the production of glucose.

In the saccharification of starch with a glucoamylase, it has been known that when the reaction of saccharification is carried out in the presence of a pullulanase possessing an ability to hydrolyze the α-1,6-glucosidic bond, it is promoted so much as to increase the yield of glucose by 0.5 to 2% (Japanese Patent Publications SHO No. 54(1979)-29570, SHO No. 57(1982)-39, SHO No. 57(1982)-174089, etc.) An increase in the yield of glucose can also be attained by the use of a certain kind of α-amylase (Japanese Patent Publication SHO No. 61(1986)-19498). Pullulanase in an enzyme capable of hydrolyzing the α-1,6-glucosidic bond of not only pullulan but also amylopectin or derivative thereof. It produces maltotriose eventually from pullulan. The pullulanase, however, is known to produce a reverse synthetic action. By virtue of this action, this enzyme produces polymerized compounds such as a compound having six glucose units combined with one another, etc. from maltotriose, for example. When the pullulanase is additionally used in the saccharification of starch with glucoamylase, therefore, there is entailed a disadvantage that the saccharification gives rise to oligosaccharides of high molecular weights sparingly hydrolyzable with a glucoamylase owing to the reverse synthetic action inherent in the pullulanase, though the saccharification brings about a recognizable addition to the yield of glucose.

OBJECT AND SUMMARY OF THE INVENTION

An object of this invention is to provide a method for the production of glucose, which method permits an addition to the yield of glucose and, at the same time, ensures formation of a sugar solution containing higher molecular oligosaccharides in an amount smaller than the amount thereof obtained by the use of pullulanase.

To be specific, the present invention is directed to a method for the production of glucose by the saccharification of liquefied starch with a glucoamylase, which method is characterized by the saccharification being carried out in the presence of a sugar transferase capable of effecting the transfer reaction with the α-1,4-glucosidic bond.

When the saccharification proceeds in the presence of a sugar transferase as described above, since the sugar is converted through the hydrolysis of saccharification produce and the transfer of sugar into a substrate easily hydrolyzable with glucoamylase, the ratio of the hydrolysis of sugar is improved and the yield of glucose is improved.

The above and other objects and features of the invention will become more apparent from the following detailed description with reference to the accompanying drawings.

DETAILED DESCRIPTION OF THE PREFERRED EMBODIMENT

The inventor, while studying saccharification of starch with a glucoamylase, searched for a new enzyme effective in increasing the yield of glucose. He has consequently found that the enzyme produced by a microorganism isolated from soil and identified as a species of genus Bacillus exhibits a conspicuous effect in enhancing the yield of glucose. When this enzyme is caused to act on soluble starch, it gives rise to a saccharified product having maltose and higher molecular maltooligosaccharides. When the enzyme is caused to act on a maltooligosaccharide of a higher order than maltose, it gives rise to maltooligosaccharides of smaller molecular weights and various maltooligosaccharides of larger molecular weights. Thus, the enzyme has been recognized to be a sugar transferase capable of effecting hydrolysis and sugar transfer at the same time. When this enzyme is caused to act on maltotriose (G3), for example, there are formed a series of maltooligosaccharides such as maltose (G2), maltotetraose (G4), maltopentaose (G5), and maltohexaose (G6), etc. which have a glucosyl group coupled with an α-1,4-glucosidic bond. It produces glucose only sparingly.

Figure 1:
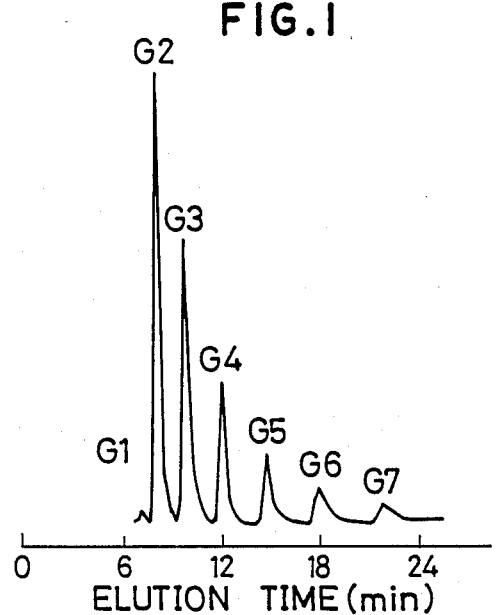
FIG. 1 is a liquid chromatogram showing the sugar composition of the product obtained by the action of a sugar transferase of Bacillus megaterium on 1% maltotriose.

FIG. 1 is a liquid chromatogram showing the amounts of maltose to maltoheptaose (G7) produced by the action of this enzyme upon 1% maltotriose. This enzyme further produces maltooligosaccharides of higher molecular weights.

4-α-D-glucanotransferase (EC 2.4.1.25) has been well known as an enzyme capable of exerting a very similar action. This enzyme is considered to fall under the same category as α-4-D-glucanotransferase. The fact that a sugar transferase of this kind is effective in increasing the yield of glucose produced by the saccharification of starch with a glucoamylase, however, has not been known to the art. It has been discovered for the first time by the present inventor. The present invention has been accomplished based on this finding.

To be specific, this invention is directed to a method for the production of glucose by the saccharification of liquefied starch with a glucoamylase, which method is characterized by the fact that the saccharification is carried out in the presence of a sugar transferase capable of effecting the transfer reaction with the α-1,4-glucosidic bond.

Now, the present invention will be described more specifically below with reference to the sugar transferase produced by the microorganis, Bacillus megaterium.

The sugar transferase of the present invention possesses the following enzymatic properties.

(1) Action

When this enzyme is caused to act on soluble starch, amylose, or amylopectin, for example, it produces a series of maltooligosaccharides such as maltose, maltotriose, maltotetraose, maltopentaose, and maltohexaose, etc. It, however, produces glucose sparingly. When the enzyme is caused to act on a maltooligosaccharide of an order higher than maltotriose, it produces a series of maltooligosaccharides higher in order than maltose but produces glucose only sparingly.

FIG. 1 shows the amount of sugars up to maltoheptaose (G7) produced by the action of this enzyme on 1% maltotriose. The products obtained included oligosaccharides of still higher molecular weights. When the enzyme is caused to act on a maltooligosaccharide of an order higher than maltotetraose, it is found to produce various maltooligosaccharides of a similar composition. These facts lead to the conclusion that this enzyme is a sugar transferase which by the simultaneous action of hydrolysis and transfer effects what may well be termed as disproportion of substrate molecule, viz. formation of maltooligosaccharides of smaller molecular weights and maltooligosaccharides of larger molecular weights from the substrate molecule. As an enzyme capable of exerting a very similar action, 4-α-D-glucanotransferase (EC 2.4.1.25) has been known to the art. The enzyme of the present invention is considered to be classified under the same category as the enzyme, EC 2.4.1.25. This enzyme, where maltotriose is used as a substrate, produces glucose [and is utilized, by virtue of this behavior, for the determination of activity ("Enzyme Handbook", page 272, complied by Shiro Akabori et al. and published by Asakura Shoten]. In the case of the enzyme of this invention, however, it produces glucose sparingly as clearly noted from FIG. 1. During the early stage of the transfer reaction, it mainly produces maltose and maltotetraose. This fact indicates that the transfer of sugar caused by this enzyme occurs mostly on the glucosyl unit. This enzyme acts also on maltose, though slightly, and produces various maltooligosaccharides having larger molecular weights than maltose. When it is caused to act on maltopentaose, it starts producing maltotetraose (G4) in a relatively early stage of the reaction, then proceeds to produce maltotriose (G3) and maltose (G2), and goes on producing, as products of transfer reaction, maltohexaose (G6), maltoheptaose (G7), maltooctaose (G8), and so on. The enzyme acts on high-molecular soluble starch and also acts on pullulan and produces reducing sugars. Thus, the enzyme is considered to take water as an acceptor.

(2) Working pH and optimum pH

Figure 3:
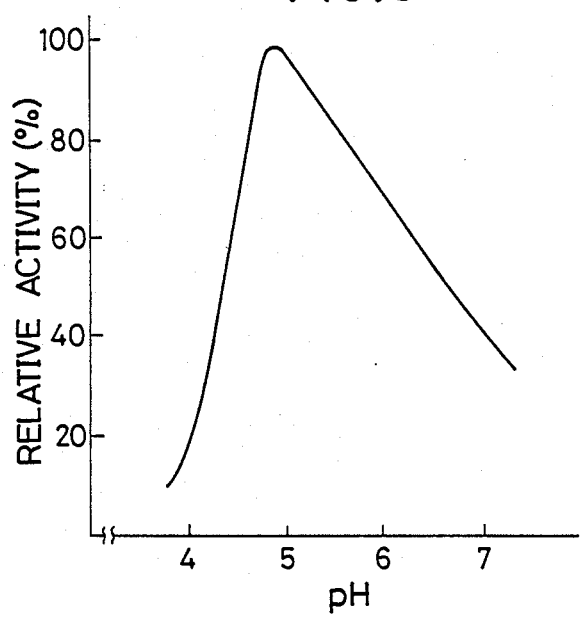
FIG. 3 is a graph showing the relation between the pH and relative activity of the sugar transferase.

The enzyme operates effectively in a wide range of pH values from about 3 to about 9, optimally in the neighborhood of pH 5 (as shown in FIG. 3 indicating the results of one hour's reaction of the enzyme on 1% soluble starch at 50° C. in the presence of a 0.1M acetate buffer solution or phosphate buffer solution and $1 \times 10^{-2}$M calcium chloride).

(3) Working temperature and optimum temperature

Figure 4:
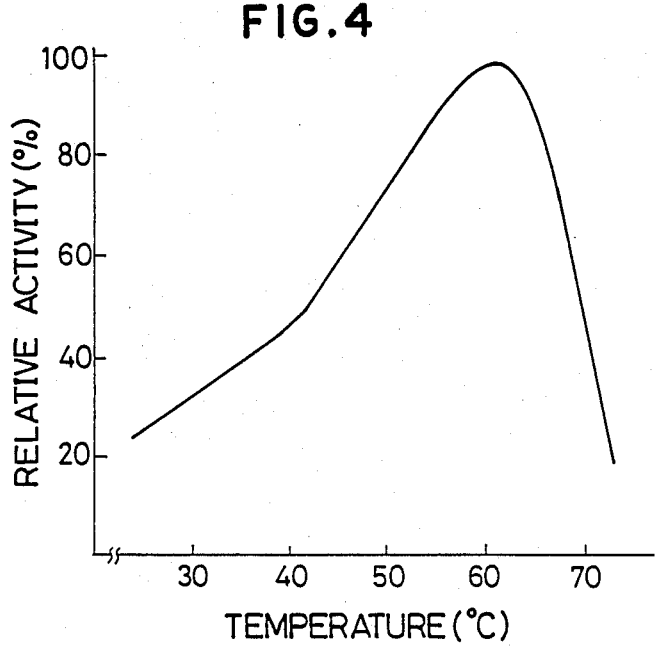
FIG. 4 is a graph showing the relation between the temperature and relative activity of the sugar transferase.

The enzyme effectively operates at temperatures up to about 80° C. and is found to operate optimally in the neighborhood of 60° C. [as shown in FIG. 4 indicating the results of 30 minutes' reaction of the enzyme on 1% soluble starch in the presence of a $2.5 \times 10^{-2}$M acetate buffer solution (pH 5)].

(4) Thermal stability

When an aqueous solution of this enzyme is heat-treated at 50° C., 55° C., and 60° C. each for 10 minutes and then tested for residual activity, it is inactivated respectively by about 0%, about 30%, and about 80%. At 50° C., the heat treatment continued for 30 minutes is found to bring about practically no inactivation of the enzyme.

(5) pH stability

This enzyme is stable in a pH range of about 4.5 to about 7 (as determined by allowing a sample to stand at room temperature for three hours in the presence of a $5 \times 10^{-2}$M acetate buffer solution or tris-buffer solution and measuring the residual activity at the end of the standing).

(6) Stabilizer and activator

This enzyme is stabilized in the presence of a calcium or iron ion. Further, a calcium ion even enhances the activity of the enzyme.

(7) Inhibitor

This enzyme is strongly inhibited by a $1 \times 10^{-3}$M copper, mercury, or silver ion.

(8) Molecular weight

The enzyme is found by the gel filtration method using Sephadex G-200 to have a molecular weight of about 500,000.

(9) Method for purification

This enzyme can be purified to the degree of homogeneity by combining the supernatant of culture broth of the microorganism with ammonium sulfate to 70% saturation, collecting the precipitate portion consequently formed by centrifugal separation, dialyzing and concentrating the collected precipitate, and subjecting the concentrate to column chromatography using Sephadex G-200 and to re-chromatography using the same column.

(10) Method for determination of enzyme activity

A suitable amount of the enzyme is added to 0.5 ml of a solution of 2% soluble starch (or pullulan) in a 0.1M acetate buffer solution (pH 5.0) containing $1 \times 10^{-2}$M calcium chloride, filled up the resultant mixture with distilled water to a total volume of 1 ml, and allowing the mixture to react at 60° C. The amount of the enzyme required to produce a reducing power corresponding to 1 $\mu$M of glucose per minute is defined as 1 A unit (or as 1 P unit where pullulan is used as the substrate). In the case of purified enzyme, the ratio of P unit/A unit is about $\frac{1}{4}$.

The reaction for saccharifying starch with glucoamylase by the additional use of the enzyme of the present invention is generally carried out with a liquefied starch concentration of 30 to 35 (W/V)%, at a pH of 4 to 5 and a temperature of 55° to 60° C., for two or four days.

The amount of the enzyme of this invention to be added is generally about 0.1 to 1 P unit/gram of starch. In general the addition of the enzyme to the starch is effected simultaneously with the addition of glucoamylase.

As starch used as a material for saccharification, dextrin obtained by liquefying starch with α-amylase produced by genus Bacillus can be used advantageously. The concentration of the material for saccharification is generally in the range of about DE 10 to about DE 15.

Table 1 shows the effect of the enzyme of this invention on the yield of glucose produced by 72 hours' saccharification of 30% dextrin (DE 13) with a commercially available glucoamylase of genus Aspergillus niger at pH 4.5 at a temperature of 60° C. in comparison with that of glucoamylase alone and that of a combination of glucoamylase and commercially available pullulanese of genus Bacillus.

was carried out in the presence of the enzyme of the present invention. This improved yield nearly equal the yield (97.2) obtained by the use of a combination of glucoamylase and pullulanase. Thus, the enzyme of the present invention is characterized by producing trisaccharide (G3) and higher saccharides less than pullulanase.

When an oligosaccharide of high molecular weight is present in the saccharification solution, it degrades the filtrability of the sugar solution and causes suspension of clouding particles in the sugar solution. The saccharification solution, therefore, is desired to have as small as high molecular oligosaccharide content as possible. In this respect, the enzyme of the present invention has an advantage that it is effective in ensuring production of a sugar solution having a small high molecular oligosaccharide content in addition to enhancing the yield of glucose.

Figure 2:
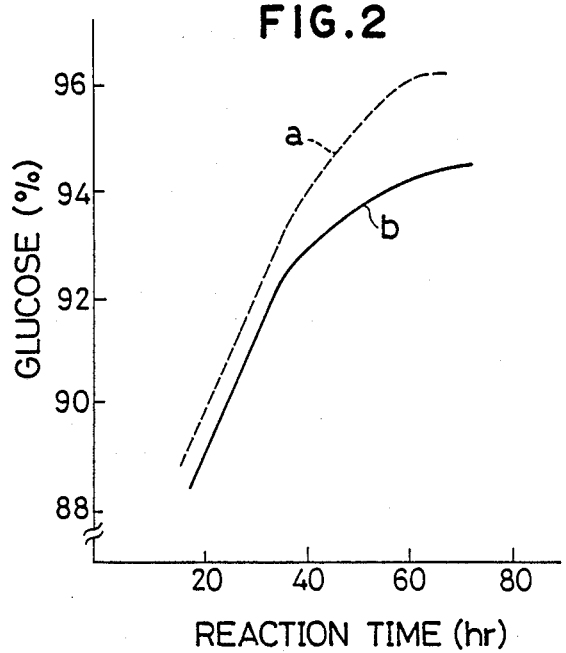
FIG. 2 is a graph showing the relation between the amount of glucose formed and the reaction time observed during the saccharification of liquefied starch with a glucoamylase in the presence of the sugar transferase.

FIG. 2 shows time-course changes of saccharification of liquefied starch obtained when glucoamylase was used alone and when it was used in combination with the enzyme of this invention. As noted clearly from the diagram, the presence of this enzyme was effective in promoting the saccharification. This fact implies that this enzyme permits a saving in the amount of glucoamylase to be used. In the saccharification of starch with glucoamylase, the enzyme of the present invention is considered to play the following role. It is known that the affinity (reactivity) of glucoamylase for the substrate is affected largely by the polymerization degree of glucose. The affinity is larger for a substrate having a larger molecular weight than for a substrate having a smaller molecular weight. In the latter stage of the saccharification of starch with a glucoamylase, there are formed oligosaccharides of various molecular weights not easily hydrolyzable with glucoamylase. The enzyme of the present invention is capable of providing a substrate easily hydrolyzable with glucoamylase through the transferase action and, consequently is capable of improving the ratio of hydrolysis and increasing the yield of glucose. An enzyme capable of manifesting the transferase action as mentioned above ought to make an addition to the yield of glucose similarly to the enzyme of this invention. The α-amylase of Bacillus subtilis, Bacillus licheniformis, or Aspergillus oryzae which lacks the transferase action is not found to be effective in increasing the yield of glucose.

Use of the pullulanase is believed to make up for the poor ability of glucoamylase to sever the branch bond α-1,6-glucosidic bond), thereby promoting of the reaction of saccharification. Thus, the pullulanase differs from the enzyme of this invention in the mechanism for the enhancement of the yield of glucose. It is, therefore, logical to conclude that the products of saccharification of starch obtained by the two enzymes are different in sugar composition.

The microorganism, Bacillus magaterim, which pro-

TABLE 1

| Sugar component | Control (only glucoamylase) | Glucoamylase + pullulanase | Glucoamylase + enzyme of the invention |
| --- | --- | --- | --- |
| G1 | 95.2(%) | 97.2(%) | 97.1(%) |
| G2 | 1.7 | 1.7 | 2.2 |
| G3 | trace | 0.3 | 0.2 |
| G4 | 3.0 | 0.8 | 0.5 |

It is clearly noted from the table that while the yield of glucose was only 95.2% where glucoamylase was used alone, it rose to 97.1% where the saccharification duces the sugar transferase of this invention possesses the following mycological properties.

(1) Form: Rods, motile.
(2) Spore: Sporagium not swelled; spore elliptic; position central to sub terminal.
(3) Gram's stain: +
(4) Catalase: +
(5) V-P reaction: −, pH 5.0
(6) Growth under anaerobic conditions: −
(7) Hydrolysis of starch: +
(8) Liquefaction of gelatin: +
(9) Reaction with egg yolk: −
(10) Acid production with glucose: +
(11) Gas production with glucose: −
(12) Growth at pH 5.7: +
(13) Growth at 50° C: −
(14) Citrate utilization: +
(15) Growth in presence of 5% NaCl: +
(16) Reduction of acetate: −

By comparing the foregoing mycological properties with Bergey's Manual of Determinative Bacteriology, 8th edition (The William & Wilkins Co., 1974), the microorganism has been identified to be Bacillus megaterium. This microorganism was deposited at Fermentation Research Institute, Agency of Industrial Science and Technology, Ministry of International Trade and Industry, under FERM BP-1672 on Jan. 26, 1988. For the production of the enzyme of the present invention by the use of this microorganism, such organic nitrogen sources as peptone, meat extract, yeast extract, and corn steep liquor, such inorganic nitrogen compounds as urea, ammonium chloride, ammonium sulfate, ammonium phosphate, sodium nitrate, potassium nitrate, and such carbon sources as soluble starch, dextrin, sugar, maltose, and glucose are used. In a culture medium containing small amounts of phosphate, magnesium salt, and calcium salt in addition to those mentioned above and adjusted to pH 5 to 8, the microorganism is aerobically cultured at 30° C. for one to four days. The enzyme is produced substantially extracellularly. After completion of the culture, the culture broth is filtered or centrifuged to remove the cells. The supernatant is then concentrated, salted out and precipitated with sodium sulfate or ammonium sulfate, or treated with an organic solvent such as methanol, ethanol, propanol, isopropanol, or acetone, to recover the enzyme.

In addition to the sugar transferase, the microorganism produces a maltose-producing amylase. This amylase is of no effect in enhancing the yield of glucose and interferes with the measurement of the activity of the present enzyme. In the case of the culture broth or the crude enzyme, the content of the enzyme of this invention therein can be accurately determined by using pullulan as a substrate.

As is plain from the fore going description, in a process for the saccharification of starch into glucose with a glucoamylase, the transferase placed in the reaction system enhances the yield of glucose and permits production of a sugar solution having a small high molecular weight oligosaccharide content.

Now, the present invention will be described more specifically below with reference to working examples. It should be noted, however, that this invention is not limited to the following examples.

EXAMPLE 1

In an Erlenmeyer flask having an inner volume of 2 liters, 300 ml of a culture medium (pH 5) containing 2% of polypeptone, 2% of soluble starch, 0.3% of $K_2HPO_4$, and 0.1% of $MgSO_4 \cdot 7H_2O$ was sterilized by the conventional method. Then, a strain of Bacillus megaterium FERM BP-1672 was inoculated and cultured by shaking at 30° C. for four days.

After completion of the culture, the culture broth was centrifuged and the supernatant consequently obtained was assayed to determine the amount of enzyme formed therein. The amount of the product was 1.5P units per ml of the culture medium.

The supernatant obtained after completion of the culture was saturated to 70% with ammonium sulfate. The precipitate consequently formed was collected by centrifugation, dissolved in distilled water, and dialyzed against distilled water. The dialyzate was used in the following test for saccharification.

EXAMPLE 2

Commercially available dextrin [liquefied starch (DE about 13), with Bacillus α-amylase produced by Nippon Shiryo K.K. and marketed under product code of "NSD"] was used as a substrate and a product of Aspergillus niger origin marketed by Nippon Finne Sugar K.K. as a glucoamylase. As a pullulanase, a product of Bacillus acipopululiticus origin marketed by Novo Japan K.K. was used. The composition of the reaction solution was as shown in Table 2.

TABLE 2

| Sample | Substrate (g) | Glucoamylase (% based on solids) | Pullulanase (P unit/g) | Enzyme of the invention (P unit/g) |
|---|---|---|---|---|
| 1 | 3.3 | 0.1 | 0 | 0 |
| 2 | 3.3 | 0.1 | 0.25 | 0 |
| 3 | 3.3 | 0.1 | 0 | 0.25 |

Each sample 10 ml in total volume was saccharified at pH 4.5 at 60° C. for 65 and 72 hours (in the sample using the enzyme of this invention, $CaCl_2$ was added at a concentration of $1 \times 10^{-2}M$). The saccharification solution consequently obtained was analyzed by high speed liquid chromatography. The results are shown in Table 3.

TABLE 3

| | Time of saccharification (hr.) | | | | | |
|---|---|---|---|---|---|---|
| | 65 | | | 72 | | |
| Sample | 1 | 2 | 3 | 1 | 2 | 3 |
| G1 (%) | 95.1 | 96.7 | 96.6 | 95.2 | 97.2 | 97.1 |
| G2 (%) | 1.7 | 1.8 | 2.1 | 1.7 | 1.7 | 2.2 |
| G3 (%) | trace | 0.4 | 0.3 | trace | 0.3 | 0.2 |
| G4 or more (%) | 3.2 | 1.1 | 1.0 | 3.0 | 0.8 | 0.5 |

From this table, it is noted that in the sample using the enzyme of this invention, the yield of glucose was about 2% higher than in the sample using glucoamylase alone. The increase in the yield was roughly the same as when a pullulanase was used. In the sample using the enzyme of the present invention, the disaccharide was produced slightly more and the trisaccharide and other higher saccharides were produced less than in the sample using pullulanase.

EXAMPLE 3

A mixture consisting of 3 g as solids of a liquefied starch (DE about 13) obtained by saccharifying maize starch with a Bacillus α-amylase and 0.1% of glucomaylase per solid and a mixture further consisting of 0.75P unit of the enzyme prepared in Example 1 and $1 \times 10^{-2}M$ of $CaCl_2$ were left reacting at pH 4.5 at 60° C. respectively. In the course of the reaction, each of the reaction solutions was sampled at fixed intervals and assayed for glucose by liquid chromatography. The results are shown in FIG. 2. It is clearly noted by the diagram that in the sample containing the enzyme of this invention (Curve a), the saccharification was promoted as compared with the sample containing glucoamylase alone (Curve b). In the former sample, glucose was obtained in a higher yield than in the latter sample.

What is claimed is:

1. A method for the production of glucose, comprising:

adding a glucoamylase and a transferase to liquefied starch, thereby saccharifying said liquified starch, wherein said transferase attains a transfer reaction with an α-1,4-glucosidic bond of said liquified starch.

2. The method according to claim 1, wherein said transferase is an enzyme possessing the ability of 4-α-D-glucanotransferase.

3. The method according to claim 1, wherein the source for said transferase is a microoganism of genus Bacillus.

4. The method according to claim 2, wherein the source for said transferase is a microorganism of genus Bacillus.

5. The method according to claim 3, wherein said microorganism of genus Bacillus is Bacillus megaterium FERM BP-1672.

6. The method according to claim 4, wherein said microorganism of genus Bacillus is Bacillus megaterium FERM BP-1672.

7. The method according to claim 1, wherein the amount of said transferase is in the range of 0.1 to 1.0 P unit per gram of starch.

8. The method according to claim 2, wherein the amount of said transferase is in the range of 0.1 to 1.0 P unit per gram of starch.

9. A method for the production of a transferase, which comprises aerobically culturing a transferase-producing microorganism of genus Bacillus in a culture medium containing a nitrogen source and a carbon source at pH 5 to 8 at 30° C. and collecting said transferase from the resultant culture broth.

10. The method according to claim 9, wherein said microorganism of genus Bacillus is Bacillus megaterium FERM BP-1672.

* * * * *